United States Patent
Atala et al.

(10) Patent No.: US 6,673,339 B1
(45) Date of Patent: *Jan. 6, 2004

(54) PROSTHETIC KIDNEY AND ITS USE FOR TREATING KIDNEY DISEASE

(75) Inventors: Anthony Atala, Weston, MA (US); James J. Yoo, Brookline, MA (US); Samy Ashkar, Boston, MA (US)

(73) Assignee: Children's Medical Center Corporation, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/254,476
(22) PCT Filed: Sep. 4, 1997
(86) PCT No.: PCT/US97/15470
§ 371 (c)(1), (2), (4) Date: May 26, 1999
(87) PCT Pub. No.: WO98/09582
PCT Pub. Date: Mar. 12, 1998

Related U.S. Application Data
(60) Provisional application No. 60/025,511, filed on Sep. 5, 1996.

(51) Int. Cl.[7] .............................................. A01N 63/00
(52) U.S. Cl. ................... 424/93.2; 623/23.65; 623/915; 435/401
(58) Field of Search ........................... 623/23.65, 23.64, 623/23.68, 23.76, 915; 435/325, 373, 401, 395; 424/93.2

(56) References Cited

U.S. PATENT DOCUMENTS

| | | | |
|---|---|---|---|
| 4,769,037 A | 9/1988 | Midcalf | 623/12 |
| 5,092,886 A * | 3/1992 | Dobos-Hardy | 623/23.65 |
| 5,429,938 A | 7/1995 | Humes | 435/240.2 |
| 5,516,680 A | 5/1996 | Naughton et al. | 435/240.243 |
| 5,545,131 A * | 8/1996 | Davankov | 604/5.04 |
| 5,549,674 A | 8/1996 | Humes et al. | 623/11 |

FOREIGN PATENT DOCUMENTS

| GB | 2011274 | 7/1979 |
|---|---|---|
| WO | 9307913 | 4/1993 |

OTHER PUBLICATIONS

Ashkar, S. et al., "Regulation of Gluconeogenesis in Swine Kidney Proximal Tubule Cells," *Molecular and Cellular Biochemistry*, vol. 87, 105–118 (1989).

Boogaard, P.J. et al., "Renal Proximal Tubular Cells in Suspension or in Primary Culture as In Vitro Models to Study Nephrotoxicity," (ABST) *Chem. Biol. Interact*, vol. 76, No. 3, 251–91 (1990).

(List continued on next page.)

*Primary Examiner*—Corrine McDermott
*Assistant Examiner*—Brian E Pellegrino
(74) *Attorney, Agent, or Firm*—Thomas Engellener; Jasbir Sagoo; Nutter, McClennen & Fish, LLP

(57) ABSTRACT

The invention is directed to a prosthetic kidney, to methods of making a prosthetic kidney and to methods of treating kidney disease with a prosthetic kidney. The prosthetic kidney comprises nephron analogs on the exterior surface and an enclosed porous membrane structure equipped with an effluent channel for collecting and draining urine from the device. The nephron analogs are prepared by implanting a device containing renal tubule analogs on the membrane structures and inducing angiogenesis to form glomeruli-like structures. The renal tubule analogs are prepared by seeding kidney cells on the porous membrane structure and culturing this composite in vitro.

18 Claims, 7 Drawing Sheets

OTHER PUBLICATIONS

Courjault–Gautier, F. et al., "Consecutive use of Hormonally Defined Serum–free Media to Establish Highly Differentiated Human Renal Proximal Tubule Cells in Primary Culture," (ABST) *J. Am. Soc. Nephrol.*, vol. 5, No. 11, 1949–63 (May 1995).

Fournier, N. and Doillon, C.J., "Biological Molecule–impregnated Polyester: An In Vivo Angiogenesis Study," (ABST) *Biomaterials*, vol. 17, No. 17, 1659–65 (1996).

Genestie, I. et al., "Polarity and Transport Properties of Rabbit Kidney Proximal Tubule Cells on Collagen IV–coated Porous Membranes," (ABST) *Am. J. Physiol.*, vol. 269, No. 1, pt. 2, f22–30 (Jul. 1995).

Humes, H.D. et al., "Effects of Transforming Growth Factor–$\beta$, Transforming Growth Factor–$\alpha$, and Other Growth Factors on Renal Proximal Tubule Cells," *Laboratory Investigation*, vol. 64, No. 4, 538–45 (1991).

Humes, H.D. et al., "Tubuolgenesis From Isolated Single Cells of Adult Mammalian Kidney—Clonal Analysis With a Recombinant Retrovirus," (ABST) *American Journal of Physiology–Renal Fluid and Electrolyte Physiology*, vol. 40, No. 1, f42–9 (Jul. 1996).

Taub, M. et al., "Epidermal Growth Factor or Transforming Growth Factor $\alpha$ is Required for Kidney Tubulogenesis in Matrigel Cultures in Serum–free Medium," *Proc. Natl. Acad. Sci.*, vol. 87, 4002–6 (May 1990).

* cited by examiner

PROSTHETIC KIDNEY AND ITS USE FOR TREATING KIDNEY DISEASE

This application claims the benefit of provisional application 60/025,511 filed Sep. 5, 1996.

BACKGROUND

1. Field of the Invention

The invention is directed to a prosthetic kidney, to methods of making the prosthetic kidney and to methods of treating kidney disease with the prosthetic kidney.

2. Description of the Background

The kidneys remove metabolic wastes from the blood, control fluid balance by maintaining homeostasis, and provide important regulatory activities by secreting hormones. Normally about 20% of the blood pumped by the heart is treated by the kidneys.

Nephrons, the functional unit of the kidneys, treat blood by three processes: filtration, reabsorption, and secretion. Each kidney contains about one million nephrons, each consisting of a renal corpuscle and a renal tubule. The shape of a nephron resembles a miniature funnel with a very long convoluted stem. Blood enters the renal corpuscle, through the glomerulus. The filtrate from the blood enters the glomerular capsule, also called Bowman's capsule, and flows through the renal tubule. The renal tubule comprises four parts, the proximal convoluted tubule, the loop of Henle, the distal convoluted tubule and the collecting tubule.

The renal corpuscle comprises a tangled cluster of blood capillaries called a glomerulus which is about 200 microns in diameter surrounded by a thin walled saclike structure called a glomerular capsule. Blood enters and exits the glomerulus through the afferent and the efferent arteriole. While in the glomerulus, blood pressure causes water and various dissolved substances to be filtered out to the glomerular capillaries into the glomerular capsule as glomerular filtrate.

The relative concentration of some of the substances in plasma, glomerular filtrate and urine is shown in Table I and Table II. These values may vary depending on many factors such as fluid consumption, medication, age, diet, health and kidney function of the patient.

TABLE I

| Substance | Plasma (mEq/l) | Glomerular Filtrate (mEq/l) | Urine (mEq/l) |
|---|---|---|---|
| Sodium | 142 | 142 | 128 |
| Potassium | 5 | 5 | 60 |
| Calcium | 4 | 4 | 5 |
| Magnesium | 3 | 3 | 15 |
| Chlorine | 103 | 103 | 134 |
| Bicarbonate | 27 | 27 | 14 |
| Sulfate | 1 | 1 | 33 |
| Phosphate | 2 | 2 | 40 |

TABLE II

| Substance | Plasma (mg/100 ml) | Glomerular Filtrate (mg/100 ml) | Urine (mg/100 ml) |
|---|---|---|---|
| Glucose | 100 | 100 | 0 |
| Urea | 26 | 26 | 1820 |
| Uric Acid | 4 | 4 | 53 |
| Creatinine | 1 | 1 | 196 |

The total rate of glomerular filtration typically is about 180 liters per day per person. Most of this volume is returned to the bloodstream via the process of reabsorption. Reabsorption is the movement of substances out of the renal tubules into the blood. Substances reabsorbed comprise water, glucose and other nutrients, sodium and other ions. Reabsorption begins in the proximal convoluted tubules and continues in the loop of Henle, distal convoluted tubules and collecting tubules.

Secretion is the process by which substances and fluids move into the distal and collecting tubules from blood in the capillaries around these tubules. Substances secreted are hydrogen ions, potassium ions, ammonia, and certain drugs. Kidney tubule secretion plays a crucial role in maintaining the body's acid/base balance.

Homeostasis is maintained by the body by specialized hormones which affect the functions of the kidneys. The pituitary hormone ADH (antidiuretic hormone) decreases the amount of urine produced by making distal and collecting tubules permeable to water. Aldosterone, secreted by the adrenal gland controls the kidney tubules reabsorption of salt and other electrolytes. Primarily, aldosterone stimulates the tubules to reabsorb sodium at a faster rate.

While hormones affect kidney function, the kidneys also produce hormones to regulate the function of other organs. Erythropoietin is a hormone secreted by the kidney cells to regulate the rate of red blood cell formation. Renin, a second hormone secreted by the kidneys regulates blood pressure. In addition, the kidneys activate vitamin D, which is involved in skeletal integrity.

To summarize, blood is treated and urine is formed as a result of glomerular filtration of blood plasma, tubular reabsorption and tubular secretion. In tubular reabsorption, substances such as glucose, amino acids, proteins, creatine, lactic acid, citric acid, uric acid, ascorbic acid, phosphate ions, sulfate ion, calcium, potassium ions, sodium ions water and urea are reabsorbed. In tubular secretion, penicillin, creatinine, histamine, phenobarbital, hydrogen ions, ammonia, and potassium are secreted.

When both kidneys in a patient fail, the blood pressure may rise, fluid may collect in the body, waste levels may build up to a harmful level in the blood and red blood cell production may be reduced. When this happens, treatment is needed to replace the function of the failed kidneys. Treatments for renal dysfunction include hemodialysis, peritoneal dialysis, and kidney transplants.

Hemodialysis is a treatment procedure that cleans and filters the blood of a patient with renal inadequacy. The treatment procedure reduces the levels of harmful wastes, extra salt and fluids. Hemodialysis also helps control blood pressure and maintains the proper balance of chemicals such as potassium, sodium, and chloride in the body.

Hemodialysis uses a dialyzer, or special filter, to treat blood. During treatment, blood from a patient travels through tubes into an external dialyzer. The dialyzer filters out wastes and extra fluids and returns the newly cleaned blood into the body. A typical treatment regimen may comprise three hemodialysis treatments per week for two to four hours each time. During treatment, mobility is limited, but a patient can engage in activities which do not require excessive movements such as reading and writing.

The disadvantages of hemodialysis include side effects and complications caused by rapid changes in the patient's body fluid and chemical balance during treatment. Muscle cramps and hypotension are two common side effects. Hypotension, a sudden drop in blood pressure, may cause extreme weakness and dizziness.

It usually takes a few months for a patient to adjust to the side effects of hemodialysis. Side effects may be reduced by strict adherence to the proper diet and the consumption of medicines as directed. A proper diet helps to reduce the wastes that build up in a patient's blood and reduces the load of the kidney. A dietitian is needed to help plan meals according to a physician's instructions.

Further disadvantages of hemodialysis include high cost and frequent and lengthy travel to a dialysis center. An alternative to dialysis centers is home dialysis. A helper is required for home dialysis and both the patient and the helper require special training. In addition, space is required for storing the machine and supplies at home.

Peritoneal dialysis uses the patient's abdomen lining, the peritoneal membrane, to filter blood. A cleansing solution, called dialysate, travels through a special tube into the patient's abdomen. Fluid, wastes, and chemicals pass from tiny blood vessels in the peritoneal membrane into the dialysate. After several hours, the dialysate is drained from the abdomen, taking the wastes from the blood with it. The abdomen is then filled with fresh dialysate and the cleaning process begins again.

The dialysis procedure involves various degrees of difficulties and significant treatment times. While treatment regimens vary, they generally pose significant inconveniences. Typical treatment regimen may comprise, for example, thirty to forty minutes every four to six hours, ten to twelve hours every night, thirty-six to forty-two hours per week, or 24 hour treatment sessions. In addition, special reduced calorie, potassium restricted diets are required in addition to dialysis.

Possible complications of peritoneal dialysis include peritonitis, or infection of the peritoneum. The procedure of peritoneal dialysis comprises many steps where pathogens such as bacteria may be introduced into the body. Symptoms of peritonitis include inflammation, exudations of serum fibrin cells and pus, nausea, dizziness, fever, abdominal pain, tenderness, constipation and vomiting. To avoid peritonitis, care is needed to follow the procedure exactly. A patient needs to be trained to recognize the early signs of peritonitis. Failure to intervene quickly may lead to serious problems.

In addition to short term inconveniences and side effects, hemodialysis and peritoneal dialysis have serious long term complications. Complications such as bone disease, high blood pressure, nerve damage, and anemia may have devastating effects with time. As a result of these complications, 60% of kidney dialysis patients are unemployed and 30% are disabled. Kidney dialysis patients generally have shorter life spans and five fold higher hospitalization when compared to the general population.

Kidney transplantation is a procedure that places a healthy kidney from a donor person into a patient's body. The implanted kidney augments or replaces the blood filtering load of the patient's failing kidneys. The implanted kidney is placed between the upper thigh and abdomen. The artery and vein of the new kidney are connected to an artery and vein of the patient, and blood flows through the new kidney and makes urine. The patient's own kidneys, which may still be partially functional, are not removed, unless they are causing infection or high blood pressure.

Like dialysis, non-histocompatible transplantation is not a cure. Tissue rejection is a significant risk even with a good histocompatibility match. Immunosuppressive regimens to prevent rejection, based on drugs such as cyclosporine, remain the cornerstone of most post-transplantation care. However the pharmaceutical immunosuppressant's narrow therapeutic window between adequate immunosuppression and toxicity, as determined by the significant intrapatient and interpatient pharmacokinetic and pharmacodynamic variabilities, renders it difficult to discern effective, but minimally toxic immunosuppressive drug levels. Thus, post-transplantation care still incurs significant costs and risks.

Prolonged immunosuppressant consumption may cause side effects. The most serious is a weakened immune system, making it easier for infections to develop. Some drugs also cause weight gain, acne, facial hair, cataracts, extra stomach acid, hip disease, liver or kidney damage. Diets for transplant patients are less limiting than for dialysis patients, but a patient is still required to cut back on some foods. Sometimes even immunosuppressants cannot prevent rejection of the kidney. If rejection happens, patients will be required to employ some form of dialysis and possibly wait for another transplant.

The time it takes to locate a kidney donor varies. There are not enough cadaver donors for every person who needs a transplant and this problem is especially acute in the case of kidney transplants. Another source of kidneys are from living donors such as relatives and spouses. Transplants from genetically related living donors often function better than transplants from cadaver donors because of better histocompatibility.

Humes (U.S. Pat. No. 5,429,938) has reported a method for culturing kidney cells for in vitro tubulogenesis and ex vivo construction of renal tubules. In the method, kidney cells are cultured in the presence of tumor growth factor $\beta 1$, epidermal growth factor and all-trans retinoic acid to form three-dimensional aggregates. Among the disadvantages of the method are the requirements for administration of growth factors and the lack of glomeruli formation. Administration of growth factors to a patient may have unwanted side effects and complications. While Humes disclosed a method which may help regrowth of damaged kidney tissue, a method for construction and use of a prosthetic kidney was not disclosed.

The growth of liver (Rozga et al., Hepatology 17, 258–65) and blood (Schwartz et al., Blood 78, 3155–61) cells constrained in semiporous membrane structures has been reported. These organ structures are not suitable for prosthetic kidney construction because they do not allow for the collection and excretion of glomerular filtrate outside the body.

Naughton and Naughton (U.S. Pat. No. 5,516,680) have reported a three-dimensional kidney cell and tissue culture system. A three-dimensional structure of living stromal cells is laid down on top of a stromal support matrix. Kidney cells are layered on top of this three dimensional system and cultured.

Vacanti and Langer (WO 88/03785) have disclosed methods for culturing cells in a three-dimensional polymer-cell scaffold of biodegradable polymer. Organ cells, cultured within the polymer-cell scaffold, are implanted into a patient's body to form an artificial organ.

Overall, therefore, it is apparent that the known methods of kidney culture contain inherent defects and flaws and place specific limitations on the ability to use the culture as a prosthetic kidney because of the limitations of their design. While each of these methods has attempted to address some of the problems encountered in the construction of prosthetic kidneys, none of the disclosed methods suggests a method for the construction of an actual prosthetic kidney capable of filtering blood, producing glomerular filtrate, secretion, or reabsorption.

SUMMARY OF THE INVENTION

The present invention overcomes the problems and disadvantages associated with current strategies and designs and provides methods, and apparatus for the treatment of kidney dysfunction and failure.

One embodiment of the invention is directed to a prosthetic kidney comprising at least one artificial renal unit (ARU). The artificial renal unit comprises a porous membrane structure having an external surface defining an enclosed internal space having at least one effluent channel, and the membrane structure further having attached to the external surface thereof and in fluid communication with the enclosed internal space thereof a plurality of nephron analogs. Each of the nephron analogs comprises a renal tubule analog having vascularization forming a glomeruli-like structure in at least one region of the renal tubule analog. The renal tubule analog comprises a three-dimensional cell aggregate of kidney tubule cells, the aggregate containing a lumen in fluid communication with the internal space of the membrane structure, and wherein the kidney tubule cells in the aggregate exhibit a brush border.

Another embodiment of the invention is directed to an artificial renal unit comprising a porous membrane structure having an external surface defining an enclosed internal space having at least one effluent channel, and the membrane structure further having attached to the external surface thereof and in fluid communication with the enclosed internal space thereof a plurality of nephron analogs. Each of the nephron analogs comprises a renal tubule analog having vascularization forming a glomeruli-like structure in at least one region of the renal tubule analog. The renal tubule analog comprises a three-dimensional cell aggregate of kidney tubule cells, the aggregate containing a lumen in fluid communication with the internal space of the membrane structure, and wherein the kidney tubule cells exhibit a brush border.

Another embodiment of the invention is directed to an artificial renal unit precursor suitable for implanting in a patient with need of additional renal function comprising a porous membrane structure having an external surface defining an enclosed internal space and having at least one effluent channel. The membrane structure further having attached to the external surface thereof and in fluid communication with the enclosed internal space thereof, a plurality of renal tubule analogs. The renal tubule analogs comprise a three-dimensional aggregate of kidney tubule cells, the aggregate containing a lumen in fluid communication with the internal space of the membrane structure, and wherein the kidney tubule cells in the aggregate exhibit a brush border.

Another embodiment of the invention is directed to a method for making an artificial renal unit precursor suitable for implantation into a patient in need of additional renal function comprising the steps of providing a porous membrane structure having an external surface defining an enclosed internal space having at least one effluent channel; contacting the external surface with a suspension of kidney tissue cells; and culturing the kidney cells on the external surface in vitro to form a plurality of renal tubule analogs, the renal tubule analogs comprising a three-dimensional aggregate of kidney tubule cells, the aggregate containing a lumen in fluid communication with the enclosed space of the membrane structure, and wherein the kidney tubule cells in the aggregate exhibit a brush border.

Another embodiment of the invention is directed to a method for treating kidney disease, or augmenting renal function, in a patient comprising the steps of implanting an artificial renal unit precursor described above into the patient in an area having native vascular supply; inducing the native vascular supply to form glomeruli-like structures at the one region; and connecting the effluent channel from the membrane structure to the urinary system of the patient.

Another embodiment of the invention is directed to a porous membrane structure for a prosthetic kidney comprising, a semipermeable membrane of a biocompatible polymer with an external surface defining an internal space, and wherein the membrane structure comprises a plurality of hollow tubes in fluid communication with a header and an effluent channel on the header allowing drainage of the internal space.

Another embodiment of the invention is directed to a method for making a renal tubule analog comprising the steps of isolating kidney tissue; dissociating the kidney tissue by enzymatic treatment to form a cell suspension; culturing the kidney cell suspension in vitro; treating an enclosed porous membrane structure with extracellular matrix protein; culturing the kidney cells on the treated exterior surface of the enclosed porous membrane structure to form renal tubule analogs, wherein the renal tubule analogs comprise three-dimensional cell aggregates of kidney tubule cells, containing lumens within the interior of the aggregates; and wherein the tubule cells exhibit a brush border.

Other embodiments and advantages of the invention are set forth, in part, in the description which follows and, in part, will be obvious from this description and may be learned from the practice of the invention.

DESCRIPTION OF THE DRAWINGS

The file of this patent contains at least one drawing executed in color. Copies of this patent with color drawing(s) will be provided by the Patent and Trademark Office upon request and payment of the necessary fee.

DESCRIPTION OF THE INVENTION

Figure 1A:
FIGS. 1A–D depict various collapsible configurations for the artificial renal unit (ARU) or the porous membrane structure.
Figure 1B:
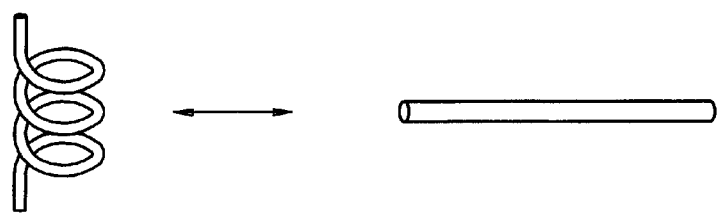
Figure 1C:
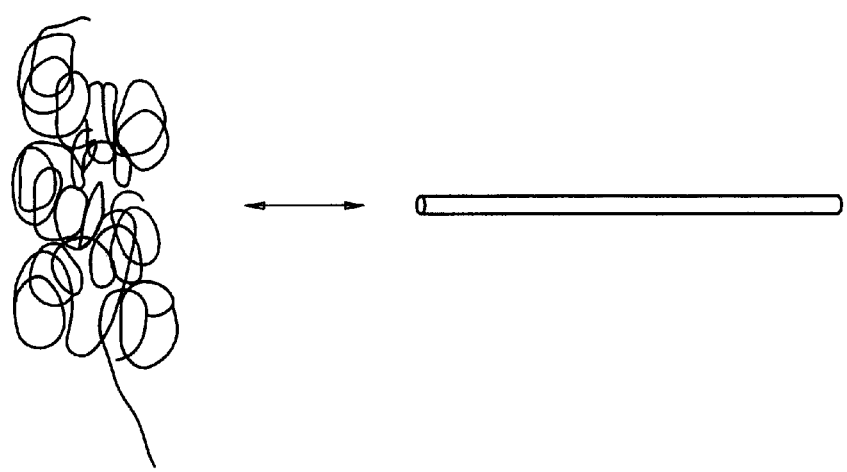
Figure 1D:
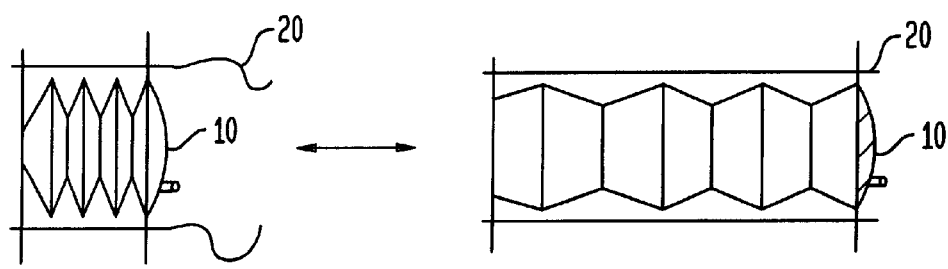

As embodied and broadly described herein, the present invention is directed to a prosthetic kidney, to methods of making a prosthetic kidney and to methods of treating kidney disease with the prosthetic kidney.

Each of the numerous methods and devices that has been used to treat kidney disease has attempted to solve one or more problems recognized as important for successful augmentation of kidney function. Examples of these methods include blood dialysis and various forms of peritoneal dialysis. However, all these methods and devices have suffered from problems related to system complexity, large size and weight, long treatment time or difficulties in controlling infections. The problems associated with current devices and methods of treating kidney diseases such as dialysis machines and intraperitoneal dialysis, include the inability to provide a high quality of life with high mobility, adequate kidney function for moderate exercise, freedom from a strict dietary regimen, and freedom from complications such as, for example, infection, nausea, pruritus, poor nutrition, pseudo gout, hepatitis B infection, accelerated cardiovascular disease, hypertension, renal osteodystrophy, anemia, pleural effusion, thrombosis, serositis, pericarditis, dialysis ascites, and dialysis dementia.

It has been demonstrated that transplanted kidneys may be effectively used on a widespread basis to treat kidney disease and that long-term survival can be obtained. However, to date, there are insufficient donor kidneys available for all patients who require one and no artificial kidney has been developed which is truly practical for widespread application. Additionally, present kidney transplant patients require a very extensive level of follow up care, including medical management of the patient's immune system.

An object of the present invention is to provide a prosthetic kidney capable of sustaining a high quality of life for many years, with a low risk of complications associated with current methods of treating kidney disease such as, vomiting, infection, hypotension, cramps, bleeding, leukopenia, hypoxia, electrolyte disturbances, and dialysis disequilibrium and nausea.

Another object of the invention is to provide a prosthetic kidney that functions effectively at high filtration rates and, therefore, occupies a reasonably small volume.

Another object of the invention is to provide prosthetic kidneys that can be implanted within the patient to replace or augment the function of the natural kidneys.

Another object of the invention is to provide a method of making prosthetic kidneys from a patient's own kidney cells or from donor cells.

Another object of the invention is to provide prosthetic kidneys that are inherently histocompatible, durable and reliable and are capable of filtrating blood for extended periods.

Another object of the invention is to provide a prosthetic kidney with redundancy to allow adequate renal function in the event of failure of one or more of its components.

Another object of the invention is to provide a prosthetic kidney comprising a biodegradable structure which may fill an initial structural role for the formation of the prosthetic kidney and then promote tissue growth as the biodegradable structure degrades.

Another object of the invention is to provide a prosthetic kidney with an effluent drainage and collection system.

One embodiment of the invention is directed to a prosthetic kidney comprising one or more artificial renal units (ARU). One preferred process for making such a device will now be described.

Harvesting Kidney Cells

The ARU is constructed in part using kidney cells from a donor. In an autologous prosthetic kidney, the kidney cells may be derived from the patient's own kidneys. In an allogeneic prosthetic kidney, the kidney cells may be derived from other member of the patient's species. In a xenogenic prosthetic kidney, the kidney cells may be derived from a species different from the patient. Donor cells may be from the cortex of the kidney of many mammalian sources such as, for example, humans, bovine, porcine, equine, caprine and ovine sources. Kidney cells may be isolated in biopsies, or autopsies. In addition, the cells may be frozen or expanded before use.

To prepare for ARU construction, a kidney or a kidney tissue section is dissociated into a cell suspension (Example 1). Dissociation of the cells to the single cell stage is not essential for the initial primary culture because single cell suspension may be reached after a period, such as, a week, of in vitro culture. Tissue dissociation may be performed by mechanical and enzymatic disruption of the extracellular matrix and the intercellular junctions that hold the cells together. Kidney cells from all developmental stages, such as, fetal, neonatal, juvenile to adult may be used.

Higher yields of cells may be obtained from fetal or neonatal tissue. To reduce stress on the cell and to facilitate handling, a section of kidney tissue may be placed in an balanced salt solution before disruption. Examples of balanced salt solutions include, for example, tissue culture medium, Hank's balanced salt solution and phosphate buffered saline and the like which are available from commercial sources such as Gibco (Gaithersburg, Md.) and Sigma (St. Louis, Mo.). The kidney tissue may be disrupted by mechanical tissue disrupter such as a scalpel, needles, scissors or a cell dissociation sieve (Sigma, St. Louis, Mo.). After mechanical disruption, the tissue may be further treated enzymatically with proteolytic enzymes such as trypsin, collagenase, dispase, and with agents that bind or chelate calcium ion such as ethylenediaminetetraacetic acid (EDTA). Calcium chelators remove the bioavailability of calcium ions on which cell-to-cell adhesion depends.

To maintain cell viability, enzymatic dissociation may be monitored by eye or by microscope. The enzymes may be inactivated after achieving desired dissociation but before cell viability is substantially impaired. Enzyme inactivation may be performed by isotonic washing, or serum treatment.

Primary cultures may be prepared from the dissociated cells with or without a cell fractionation step. Cell fractionation may be performed using techniques, such as florescent activated cell sorting, which is known to those of skill in the art. Cell fractionation may be performed based on cell size, DNA content, cell surface antigens, and viability. For example, tubule cells may be enriched and fibroblast cells may be reduced. While cell fractionation may be used, it is not necessary for the practice of the invention.

Cell sorting may be desirable, for example, when the donor has diseases such as kidney cancer or metastasis of other tumors to the kidney. A kidney cell population may be sorted to separate malignant kidney cells or other tumor cells from normal non-cancerous kidney cells. The normal non-cancerous kidney cells, isolated from one or more sorting techniques, may be used to produce a prosthetic kidney.

Another optional procedure in the method is cryopreservation. Cryogenic preservation may be useful, for example, to reduce the need for multiple invasive surgical procedures. Cells taken from a kidney may be amplified and a portion of the amplified cells may be used and another portion may be cryogenically preserved. The ability to amplify and preserve cells allow considerable flexibility in the choice of donor cells. For example, cells from a histocompatible donor, may be amplified and used in more than one recipient. An added advantage with cryopreservation and amplification is that cells from one kidney may be amplified to produce a second kidney.

Another example of the utility of cryogenic preservation is in tissue banks. Donor cells may be cryopreserved along with histocompatibility data Donor cells may be stored, for example, in a donor tissue bank. As tissue is needed to treat kidney disease in a patient, cells may be selected which are most histocompatible to the patient. Patients who have a disease or undergoing treatment which may endanger their kidneys may cryogenically preserve a biopsy of their kidneys. Later, if the patient's own kidneys fail, the cryogenically preserved kidney cells may be thawed and used for treatment. Examples of diseases which damages kidneys include, for example, high blood pressure and diabetes. Examples of kidney-damaging treatment procedures include, for example, chemotherapy and radiation.

Culturing Kidney Cells

It may be desirable to amplify the number of cells to produce sufficient starting material for the ARU. Amplification offers advantages such as reduction of the amount of donor tissue needed. For example, a small kidney biopsy section may be removed from a living donor. The removed tissue may be sufficiently small such that the donor's renal function and capacity is not substantially reduced. The removed kidney biopsy section may be amplified to provide a prosthetic kidney for one or more patients. In some situations, such as an autologous transplant where the patient has already suffered substantial kidney damage, the ability to amplify kidney cells and regenerate ARUs has substantial benefits.

Cell amplification may be accomplished by repeatedly subculturing the cells into successively larger or more numerous culture vessels. Cells may be repeatedly subcultured for weeks, months and years. Thus, one small section of kidney, for example, less than one gram of tissue from a biopsy, may after repeated culturing, be expanded into about 10 grams, about 50 grams, about 200 grams or more of tissue for use in the construction of ARUs.

In one preferred method, cells are cultured and amplified under conditions discussed in Example 2 and 3. Briefly, all cells are cultured on collagen treated plates, in Dulbecco's Modified Eagles's Medium supplemented with about 10% fetal bovine serum, about 5 $\mu$g/ml bovine insulin, about 10 $\mu$g/ml transferrin, about 10 $\mu$g/ml sodium selenite, about 0.5 $\mu$M hydrocortisone, about 10 ng/ml prostaglandin $E_2$, about 100 units/ml penicillin G, about 100 $\mu$g/ml streptomycin in an incubator at about 37° C. and about 5% $CO_2$. All media and reagents may be purchased commercially from tissue culture supply sources such as, for example, Sigma of St. Louis, Mo.

Other culture media, such as, for example, MCDB, 199, CMRL, RPMI, F10, F-12, MEM, and the like are available from commercial sources such as Gibco (Gaithersburg, Md.) and Sigma (St. Louis, Mo.) may also be used to culture kidney cells. Supplements may also be supplied by increased serum concentration such as, for example, about 15%, about 20%, about 30%, about 40% or about 50% serum. Compositions of various suitable mammalian cell media, serum, balanced salt solutions, and supplements are listed in the Gibco (Gaithersburg, Md.) and Sigma (St. Louis, Mo.) catalogs which is hereby incorporated by reference.

The culture medium and matrix used for the maintenance of viable kidney cells over long periods should be chosen in order to keep these cells in a hormonally responsive state. Small amounts of insulin, hydrocortisone and retinoic acid are desirable to maintain cells capable of forming renal tubule analogs and artificial renal units. Insulin, hydrocortisone and retinoic acid are especially desirable especially at longer culturing periods encountered during amplification of cells.

Porous Membrane Structure

The ARU of the present invention includes an enclosed porous membrane structure. This porous membrane structure comprises a porous membrane with an exterior surface defining an enclosed interior space and at least one effluent channel. As described below, renal tubule analogs are formed on the exterior surface of the porous membrane structure. In the most simple embodiment of the invention, the membrane structure may comprise a hollow tube with both ends sealed. The effluent channel may be attached to the enclosed tube to allow drainage of the interior space.

A porous membrane structure of the invention also may be, for example, a plurality of hollow porous tubes or hollow fibers, each closed at one end and in fluid communication with a header at the other end. Hollow fibers may be purchased commercially and the construction of hollow fiber for cell culture is well known to those in the art. One method of hollow fiber fabrication involves the extrusion of membrane polymers through fine dies to form tubes which harden and form tubes which are highly porous. Several hundred to several thousand to tens of thousands of fibers maybe connected to a header. Further, multiple headers may be connected by fluid channels to form a superstructure for the prosthetic kidney. Hollow fiber construction can pack a large surface to volume ratio into a relatively small volume.

Alternate porous membrane structures may comprise a plurality of hollow porous tubes or fibers open in both ends and in fluid communication at one end with a first header and in fluid communication at a second end with a second header. This design may allow flushing, or the passage of a sweeping fluid, through the porous membrane structure. Flushing may allow cleaning, disinfection, treatment, or delivery of drugs or chemicals before use and during use of the porous membrane structure.

Porous membrane structures may also be constructed by sintering-fusion of particles to form a three-dimensional structure. Other methods for the construction of porous membrane structures include casing, stretching, leaching, nucleation and laser fabrication. In casing, a thin film of solution containing the polymer and solvent is cast, sometimes on a base of cloth or paper. Solvent escapes and polymer precipitation cause pore formation. In stretching, Teflon™, polypropylene or other polymer sheets are stretched equally in all directions creating uniform pores. In leaching, a solution containing two materials is spread as a film. Next a solvent is used to dissolve away one of the components, resulting in pore formation. (See Mikos, U.S. Pat. No. 5,514,378, hereby incorporated by reference) In nucleation, thin polycarbonate films are exposed to radioactive fission products that create tracks of radiation damaged material. Next the polycarbonate sheets are etched with acid or base, turning the tracks of radiation-damaged material into pores. Finally, a laser may be used to burn individual holes through many materials to form porous membrane structures. In addition to polymeric material, metals, glasses, and ceramics may also be used to form porous membrane structure with laser fabrication. An electronic microscope may be used for quality control and to determine the structure of the membranes following any method of fabrication.

The porous membrane structures may be fabricated with natural or synthetic polymeric biocompatible materials such as cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, or copolymers or physical blends thereof. The polymer material should be selected to be compatible with, and resistant to attack by body fluids and host cells. Further, it is preferred that the material is resistant to attack by any drugs or chemicals, such as medicine or chemotherapy material which the patient may be subjected as part of the treatment of kidney disease or any other disease the patient may also have.

The porous membrane material may be biodegradable and designed to slowly degrade in a body. Biodegradable materials may fill an initial structural role for the formation of the prosthetic kidney and then promote tissue growth as they degrade. Further, it is preferred that the biodegradable material and its degraded product are non-toxic and can be easily eliminated from the system of a disease patient or a healthy patient. Representative materials for forming the biodegradable structure include natural or synthetic polymers, such as, for example, poly(alpha esters) such as poly(lactate acid), poly(glycolic acid), polyorthoesters and polyanhydrides and their copolymers, which degraded by hydrolysis at a controlled rate and are reabsorbed. These materials provide the maximum control of degradability, manageability, size and configuration.

The pores on the porous membrane structure should be sufficiently large to allow passage for fluids and gas but sufficiently small to be impermeable to cells. Suitable pore size to accomplish this objective may be about 0.04 micron to about 10 microns in diameter, preferably between about 0.4 micron to about 4 microns in diameter. Polycarbonate membranes are especially suitable because they can be fabricated in very controlled pore sizes such as, for example, about 0.01 microns, about 0.05 micron, about 0.1 micron, about 0.2 micron, about 0.45 micron, about 0.6 micron, about 1.0 micron, about 2.0 microns and about 4.0 microns. At the submicron level the porous membrane may be impermeable to bacteria, viruses and other microbes.

The porous membrane structure may be completely porous or partially porous. It may be desirable for regions of the porous membrane structure to be non-porous. Non-porous regions may include, for example, hinged regions, structural regions, effluent and affluent ports, connectors and attachment sites.

The effluent channel may be any outlet opening in the porous membrane structure such as, for example, nozzle, tube, fitting, hole, or opening or the like wherein the fluid may exit from the interior space of the porous membrane structure. Optionally, a non-refluxing valve, commonly know as a check valve, may be incorporated into the effluent channel to prevent reflux of effluent back into the porous membrane structure. A filter, with pores sufficiently large to allow passage of fluids but sufficiently small to prevent passage of microbes may be added to the effluent channel to prevent or reduce the possibility of infection of the prosthetic kidney. Optionally, means for collection and storage of effluent such as an artificial bladder, a chamber, a tube or the like may be connected to the effluent channel or the porous membrane structure. Effluent may be stored between periods of drainage or for subsequent analysis.

Figure 3A:
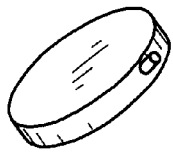
FIGS. 3A–J depict various shapes for an artificial renal unit or a porous membrane structure.
Figure 3B:
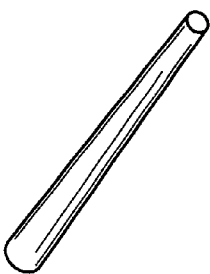
Figure 3C:
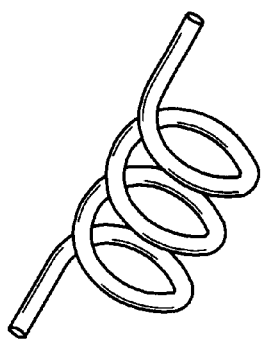
Figure 3D:
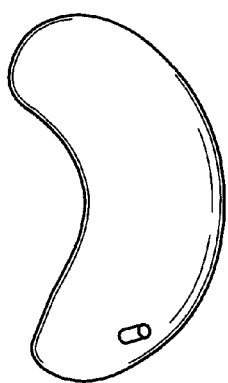
Figure 3E:
Figure 3F:
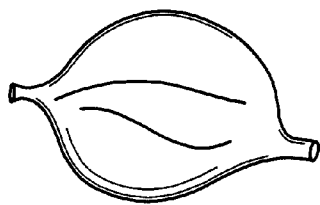
Figure 3G:
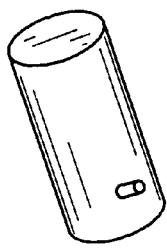
Figure 3H:
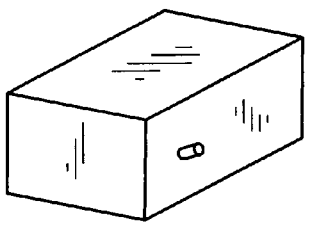
Figure 3I:
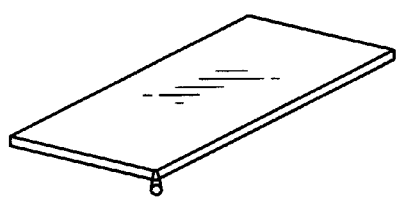

The porous membrane structure may be a collapsible structure such as, for example, the structures shown in FIG. 1. A collapsible structure is any structure that can be deployed in one shape and retracted into a second more compact shape. FIG. 1 include examples of structures which can transform shapes, such as, for example, from planar to bulbous (FIG. 1A), from elongated to helical (FIG. 1B), from elongated to superhelical (FIG. 1C) and from cylindric to bellow structures (FIG. 1D). The deployed shape may be more suitable for seeding of kidney cells or for implantation which the retracted shape may be more suitable for long term implants. The deployed shape of the collapsible porous membrane structure may be, for example, a long or flat cylinder (FIGS. 3A, 3G), an elongated tube (FIGS. 3B, 3E), a coil (FIG. 3K), a helix (FIGS. 1B and 3C), a double or multiple helix (FIG. 1C), a kidney shape (FIG. 3D), a cube (FIG. 3H), a flat bag (FIG. 3I), or combination thereof The porous membrane structure may further comprise bellows 10 (FIG. 1D), tracts, strings or wire 20 (FIG. 1D) for the pre-implantation or post-implantation deformation and shaping of the structure. Further the porous membrane structure may comprise support to maintain integrity and to prevent pressure necrosis of the cells of the ARU. Such support may comprise pillars, ribs or the like which may be attached or not attached and positioned internal or external to the porous membrane structure. The retracted shape of the collapsible porous membrane structure may be similar to the deployed shape except more complex. Other retracted shapes may comprise planes, spheres and kidney shapes. Other desirable collapsible structures may comprise retracted shapes that are designed to fit subcutaneously or within the abdomen or thorax of a patient.

Examples of collapsible structure suitable for prosthetic kidney include an accordion-like or bellows type collapsible structure (FIG. 2C), most preferably formed of a porous biocompatible polymer. Foldable or collapsible porous membrane structures can be deployed during the attachment of the kidney cells. Then the collapsible structure, in the deployed form may be implanted into a patient. As neo-angiogenic activity of the patient perfuse the prosthetic kidney, the structure may be slowly retracted. Alternatively, after attachment of kidney cells, the structure may be retracted and implanted into a patient. Collapsible three-dimensional porous membrane structures can be developed in a variety of forms. It is preferred that the three-dimensional collapsible membrane structure have a desirable final and initial geometry. Desirable geometry is dictated by the location of implantation of the prosthetic kidney. A prosthetic kidney designed to be implanted subcutaneously may be of a planar shape while a prosthetic kidney for the replacement of a normal kidney may be of a kidney shape. Another design consideration is that the structure must be deployable without causing disintegrating or component failure either in the collapsed or deployed state. For example, it is desirable for such a structure to maintain structural integrity and not to have any occlusion in the expanded and collapsed state which may cut off or reduce blood supply to the prosthetic kidney.

Figure 2A:
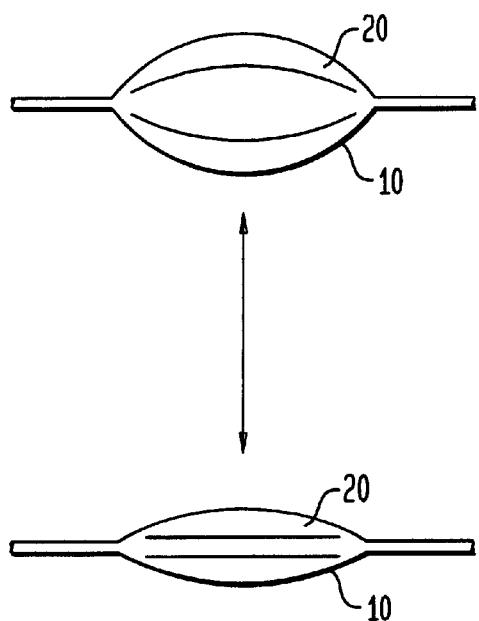
FIGS. 2A–C depict various inflatable collapsible configurations for the artificial renal unit ARU or the porous membrane structure.
Figure 2B:
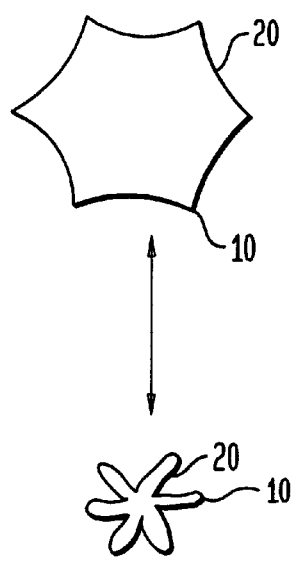
Figure 2C:
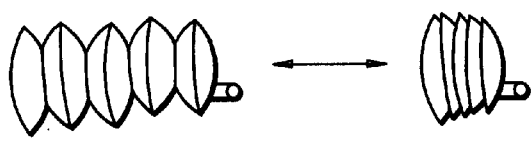

Another method for forming a collapsible porous membrane structure is an inflatable structure (FIGS. 2A, 2B, and 2C). For example one embodiment of an inflatable collapsible structure and its corresponding cross sectional structure is shown in FIGS. 2A and 2B respectively. The structure may comprise an inflatable body 10 having a flexible but substantially non-elastic and transversely convex wall 20. The transversely convex walls may be elongated and adapted to be bowed or concave and hence flexible through its width. The inflatable structure may be inflated for the seeding of kidney cells and deflated either before or after implantation. Another embodiment of an inflatable collapsible porous membrane structure is accordion shaped and shown in FIG. 2C.

Figure 3J:
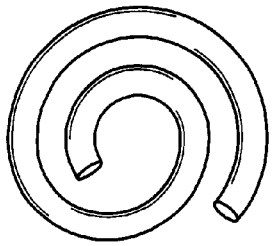
Figure 4:
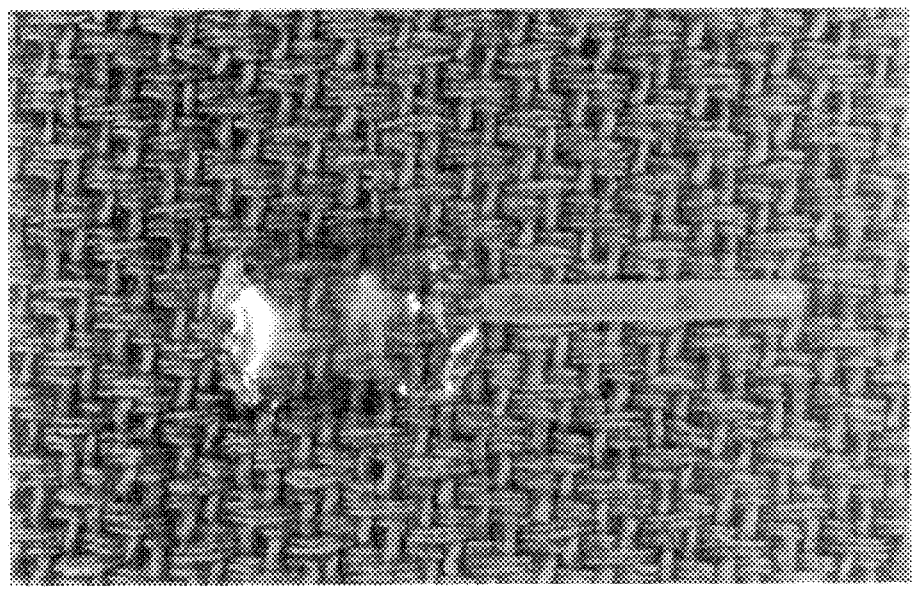
FIG. 4 depicts an artificial renal device composed of polycarbonate tubular membranes with 4 micron pore size connected to collecting ducts and a reservoir.

The enclosed porous membrane structure may optionally comprise a deformable outer casing with sufficient strength to prevent mechanical damage to the ARU. The deformable casing may be shaped into any number of desirable configurations to satisfy any number of overall system, geometry or space restrictions. The deformable casing be formed from film, gauze, webbing, wire mesh, cloth, foam rubber and the like. Suitable materials for the construction of the casing include, for example, metals such as steel, titanium, glass, polymers, fiberglass, plastic or the like. The final shape of the porous membrane structure with the outer casing may be, for example, a cylinder (FIGS. 3A, 3B, 3G), a coil (FIG. 3J), a helix (FIG. 3C), a double or multiple helix (FIG. 1C), a kidney shape (FIG. 3D), a cube (FIG. 3H), a flat bag (FIG. 3I) or combination thereof (FIG. 4). The only limitation on degree of deformation is that a significant area of the porous membrane structure and its associated ARUs not be significantly broken, stretched, crimped, or put under excessive stress, pressure, or compression such that the renal function of the prosthetic kidney is impaired, diminished or otherwise deleteriously affected.

In an embodiment of the invention, the porous membrane structure may be made with materials which are radiation resistant such that radiation therapy will not unfavorably alter the renal functions of the prosthetic kidney. In the treatment of certain diseases, such as for example, cancer of the kidneys, it may be necessary to apply radiation postoperatively. The radiation resistant porous membrane structure would permit heavy radiation to be applied with prosthetic kidney in place for residual tumor treatment if necessary.

In an embodiment of the invention, the porous membrane structure is made with materials which are ultrasound resistant. Calculi buildup and encrustation, such as for example, kidney stones, in the urinary system is a common problem among patients with reduced renal abilities. One method to treat calculi buildup, encrustations, and stones is to use ultrasonic energy to crush the buildup. An ultrasound resistant porous membrane structure will allow post-implantation ultrasound treatment without unfavorably altering the prosthetic kidney.

Another embodiment of the invention is directed to a means for delivering a drug, growth hormone and a means for controlling calculi buildup and encrustation in the porous membrane structure of the artificial renal unit (ARU) by providing at least one affluent channel to the porous membrane structure. Affluent channels may be any means which allow an introduction of solid, liquids or gas into the porous membrane structure such as a port or a fitting. Affluent channels may be positioned at a point distal from the effluent channels to allow flow of introduced fluids to pass over substantially the entire interior surface of the porous membrane structure before exiting by the effluent channel.

It is known to those of skill in the art that combinations of growth factors, such as transforming growth factor-$\beta_1$, epidermal growth factor, and all-trans retinoic acid may induce kidney tubule formation. It is also known that various chemicals and pharmaceuticals such as potassium citrate and acetohydroxamic acid inhibit crystallization of poorly soluble calcium and magnesium salts. It is known that various chemicals and pharmaceuticals such as antibiotic and metallic compounds may inhibit the growth of, or kill, microbes. Growth factors, anti-encrustation factors, and antibiotics may be added to the porous membrane structure, in liquid form, by the affluent channel. The affluent channel may further comprise for example a tube which extends from the ARU to a subcutaneous location. For example, in a patient with an abdominal ARU, the addition of growth factors, anti-encrustation factors, and antibiotics may easily be accomplished by connecting to a subcutaneously implanted inlet port accessed by a hypodermic needle.

One embodiment of the invention provides a coating of extracellular matrix material on the porous membrane structure for the growth and development of renal tubule analogs in vitro, The rapid three-dimensional growth of kidney cells for construction of ARUs may be facilitated by the availability of biomaterial matrices upon which cells can reside and regenerate. Thus, it may be preferable to treat the exterior surface of the porous membrane structure with materials that give appropriate signals for cellular growth control, such as extracellular matrix proteins.

Extracellular matrix proteins comprise glycoproteins, proteoglycans and collagen. The exterior surface of the porous membrane structure may be treated with one or a combination of these proteins. Examples of suitable extracellular proteins which may be used include collagen, fibronectin, thrombospondin, cytotactin, echinonectin, entactin, laminin, tenascin, uvomorulin, vitronectin, biglycan, chondroitin sulfate, decorin, dermatan sulfate, heparin, heparin sulfate and hyaluronic acid.

The extracellular matrix protein may be extracted freshly from a mammalian source such as rat tail. Other mammalian sources of collagen include bovine, porcine and human sources. Human extracellular protein such as collagen may be collected from human tissues such as placentae or cadavers and may be purchased from commercial suppliers such as Sigma (St. Louis, Mo.).

Extracellular matrix protein and the porous membrane structure may be sterilized prior to use. Sterilization may reduce the likelihood of microorganism contamination of the extracellular matrix protein. Preferred methods for sterilizing include ultrafiltration and radiation exposure. Radiation exposure may be, for example, gamma radiation or X-radiation exposure. Alternatively, antibiotics, antibacterials and cytotoxic agents, ultra violet radiation, in normally effective doses may be used. One preferred cytotoxic agent used is ethylene oxide.

Surface treatment of the porous membrane structure may comprise contacting a solution of ECM protein with the porous membrane structure. After contact, the pH may be raised, for example, by ammonium hydroxide to promote attachment, gelling, or polymerization. Alternatively, the extracelluar matrix protein may be crosslinked to the porous membrane structure. Crosslinking and derivatization reagents may be purchased from a commercial supplier such as Pierce (Rockford, Ill.).

Seeding Kidney Cells Onto the Porous Membrane Structure

Attachment of the kidney cells to the exterior surface of the porous membrane structure may be accomplished by combining the dissociated kidney cells with the porous membrane structure. One preferred method is described in detail in Example 3. Briefly, a porous membrane structure is gently contacted with a suspension of kidney cells at a density of about 1×10⁷ cells per square centimeter of porous membrane structure surface. The coated porous membrane structure is incubated in a tissue culture incubator under about 100% humidity, about 37° C., about 5% $CO_2$ for about 30 minutes to about one hour. After this period, medium is gently added to completely submerge the porous membrane structure.

The extracellular membrane protein on the porous membrane structure may promote attachment of kidney cells and this attachment is substantially complete within about 30 minutes to about 24 hours such as, for example, within 1 hour, 2 hours, 4 hours, 8 hours or 16 hours. The exact time required for complete attachment depends on the surface property and surface composition of the porous membrane structure, the medium, and the extracellular matrix and the kidney cells.

Culturing the Kidney Cells on the Porous Membrane Structure to Form Renal Tubule Analogs After attachment, the structure containing kidney cells is cultured in vitro for a time, and under conditions sufficient to form renal tubule analogs. For example, culture under about 5% $CO_2$ and about 37° C. for about 3 days to about 20 days, preferably between about 7 to about 10 days is generally sufficient. The medium covering the porous membrane structure may be replaced as required in time intervals of about 1 day to about 6 days, preferably between 2 days and 5 days, more preferably between 3 days and 4 days. The interval of media replacement depends on the volume of media and the rate of consumption of the nutrients in the media and the rate of accumulation of waste products. It is understood that by adjusting the volume of media, longer period such as 7 days, 8 days, 9 days or 10 days may elapse between media changes. It is understood that the addition of nutrients, antibiotics and hormones such as fetal bovine serum, insulin, transferrin, sodium selenite, hydrocortisone, prostaglandin $E_2$, penicillin, and streptomycin may extend the period between media changes.

Figure 5:
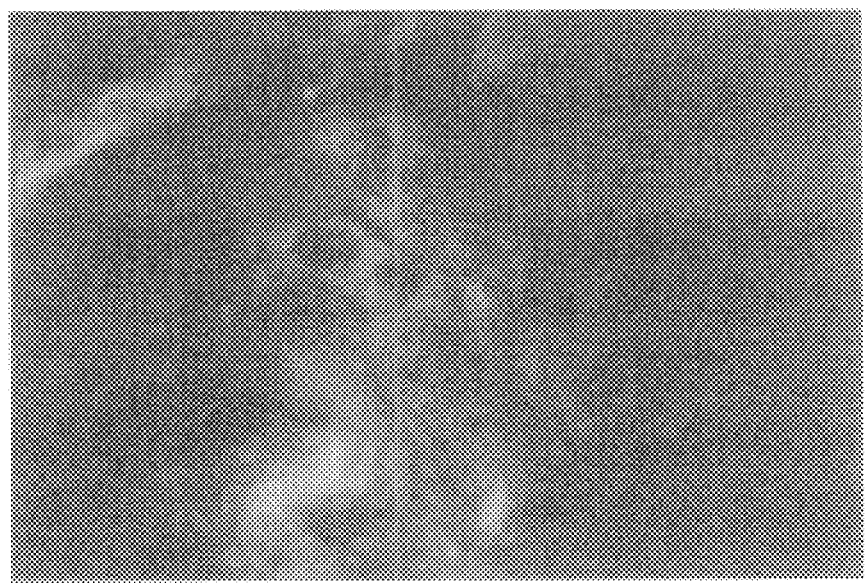
FIG. 5 depicts immunocytochemical staining of a section of artificial renal unit with anti-osteopontin antibody.
Figure 7A:
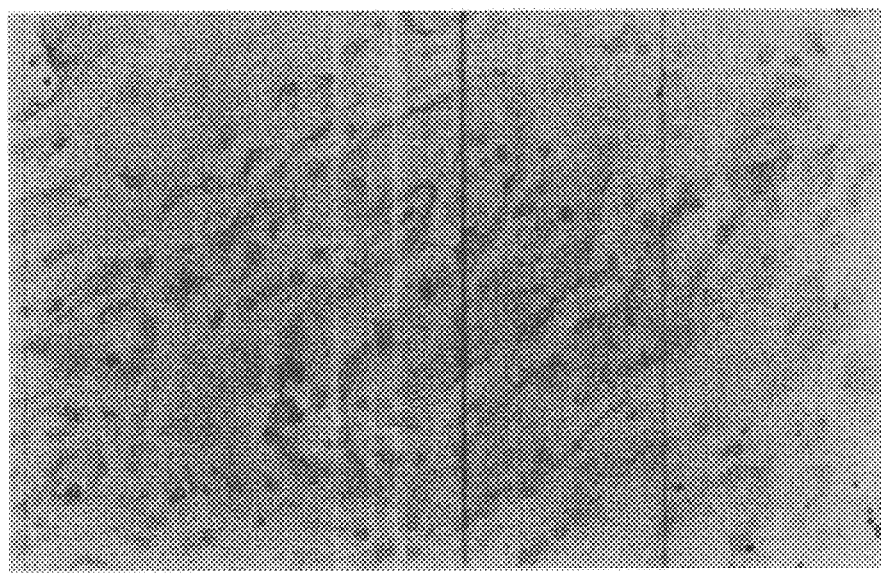
FIGS. 7A–B depict sections from an ARU stained with anti-alkaline phosphatase antibody.
Figure 7B:
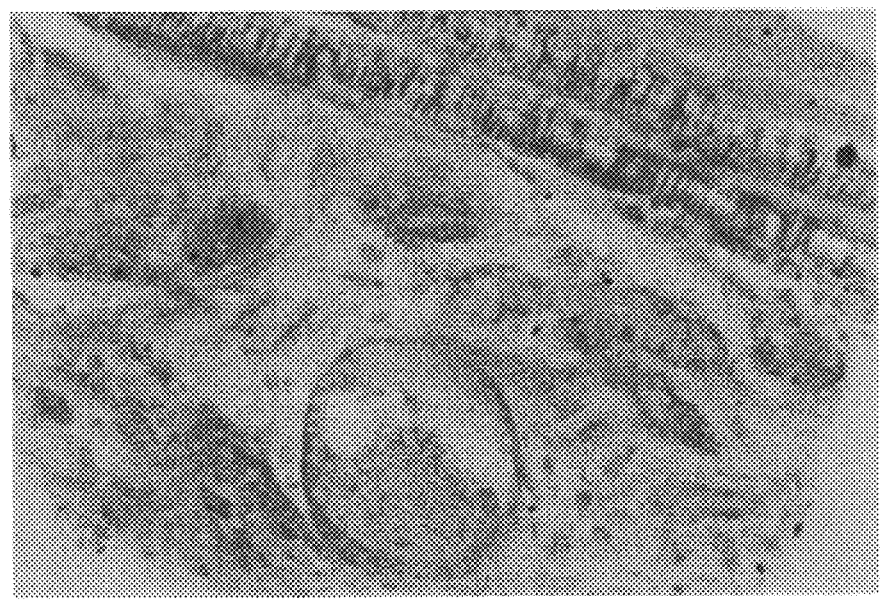

Extracellular matrix protein treatment alters the surface properties of the porous membrane structure to affect attached cell morphology and migration. When cultured on the treated porous membrane structure, kidney cells initially spread out as a monolayer, but over time spontaneously self-assemble into three-dimensional cell aggregates each comprising an interior lumen. The shape of the cell aggregates resembles a linear segment of a renal tubule. Cell aggregates are attached to the substrate and have a smooth surface with practically indistinguishable cell-cell boundaries. The renal tubule analogs may be open or closed at one end. Renal tubule analogs on a per cell basis, show higher kidney specific activities compared to the kidney cell monolayers and remain viable longer. Specific cellular functions of tubule cells include secretion, absorption, and the expression of cell specific gene products such as alkaline phosphatase (FIGS. 7A and B) and osteopontin (FIG. 5). Renal tubule analogs are attached to the porous membrane structure (FIG. 7B) and exhibit a more tissue like ultrastructure than renal cells in a monolayer.

The evolution of kidney specific activity over the course of a renal tubule analog self-assembly on the porous membrane structure may be monitored phenotypically and functionally. Phenotypically, renal tubule analogs have characteristics, such as brush border, lumens, and cell junctions similar to natural tubules. Expression of kidney tubule specific genes such as osteopontin and alkaline phosphatase may be monitored by any molecular biology or immunology methods known to those of skill in the art such as northern blots, western blots, polymerase chain protection and in situ hybridizations. Tests for activities localized to kidney proximal tubule cells such as, for example, Periodic Acid Schiff (PAS) test for glucose metabolism may be used to detect kidney proximal phenotypes.

Kidney proximal tubules were observed to form continuous sheets of oval to elongated cells on the surface the porous membrane structure. Initially, 24 hours after seeding, the kidney cells on the porous membrane structure are one cell layer thick but as they approach confluence, regions may be found in which several cell layers are present. Each cell of the renal tubule analog has a prominent round nucleus with one or two distinct nucleoli. Intracellular spaces are large with cells being attached at regions which resemble intracellular bridges. In some regions distinct infolding or pockets into the cellular surface are in evidence. Some cells contain large number of granules, presumably lysosomes, characteristic of proximal tubule cells. This granularity of the cells increased significantly in cultures which were more than 7 days old.

When examined under the microscope, renal tubule analogs, like natural tubules, show large intracellular spaces filled with long slender microvillar projections from the cell surface which resembles a brush border. Brush borders, also called striated borders are uniquely characteristic of the apical surface of the proximal kidney tubule cells. In the microscope, brush borders appear as a specialization of the free surface of a cell, consisting of minute cylindrical processes (microvilli) that greatly increase the surface area. The brush border on renal tubule analogs shows an extensive microvillar surface which is continuous into the infolding or pockets which form along the cell surface. Histology sections cut through the infolding, parallel to but below the cell surface, appear as microvillar lined channels surrounded by cytoplasm. The formation of brush border or microvilli lined pockets may represent the mechanism by which a highly microvillous cuboidal cell maintains its extensive apical surface area in an otherwise squamous cell culture environment. In regions of the cell surface lacking microvilli linked pockets or channels, the borders of cells also have long microvilli projecting from them. However, their number is reduced and their structural organization is different from the brush border observed lining the pockets or channels and adjacent surfaces. The regions of lower microvillar numbers may be the lateral and basal surfaces of normally cuboidal kidney tubule cells.

The cells of the renal tubule analogs contain the intracellular organizations typical of intact proximal tubule cells. The nuclei of the tubule cells are oval and contain scattered heterochromatin primarily at the peripherae of the nucleus. Much of the nuclear material is euchromatic in appearance and one or two nucleoli are visible upon microscopic examination. The cytoplasm of the cells of the renal tubule analogs contains numerous filamentous mitochondria often arranged parallel to the surface of the cells. The shelf like cristae are generally arranged perpendicular to the length of the mitochondrion. In the more elongated cells, fine cytoplasmic microfilament bundles and extensive networks of cytoplasmic microfilaments are also present especially in continuity with intracellular junctions. These filamentous bundles run parallel to the lateral surface of the cells. In most cells short profiles of granular endoplasmic reticulums are present although in some cells they may become very extensive. Other cellular organelles include dense lysosomal granules and prominent Golgi networks. Lysosome content may increase significantly in older culture.

Individual desmosomes can be found at sites of contact along the lateral margins of adjacent cells. Where groups of the more elongated cells make contact in a single region, very elaborate desmosome-like junctional complexes may form resembling the intercalated discs of cardiac muscle. Radiating from these complexes are extensive networks of monofilaments. These junctional complexes resemble the belt desmosomes of the apical border of normal proximal tubule cells. Thus, it is evident that on the basis of their morphology, the renal tubule analogs have all the characteristics of proximal kidney tubules.

Gene expression analysis also indicates that the renal tubule analogs express genes typical of natural tubules. Natural kidney tubules express osteopontin throughout the length of the renal tubule and express alkaline phosphatase preferentially at the proximal end. Kidney cells, as a monolayer culture exhibit very low levels of osteopontin and alkaline phosphatase activity which can be seen by the low level of staining in sections probed with anti-osteopontin and anti-alkaline phosphatase antibodies. As the kidney cells begin to aggregate into renal tubule analogs, the alkaline phosphatase activity increases. Within a single renal tubule analog, the distribution of this activity is heterogeneous. The proximal end of the renal tubule analog shows detectable levels of alkaline phosphatase. If the cells are dissociated, such as, for example, by trypsin, the cells lose their enhanced activity and return to the low levels seen in the initial monolayers. Cells which remain in a renal tubule analog structure, however, retain their enhanced activity. It is hypothesized that their enhanced cell-cell contact and more tissue-like structure contribute to the enhanced activity seen in renal tubule analogs.

Implantation of Artificial Renal Unit Precursor

The Artificial Renal Unit Precursor, which comprises an enclosed porous membrane structure with renal tubule analogs attached may be implanted into a host to induce the formation of nephron analogs by glomeruli formation at the end of the tubules. Angiogenesis is important in prosthetic kidney function. The function and growth of a prosthetic kidney require a blood supply.

In angiogenesis, the host tissue responds to signals produced by the cells of the prosthetic kidney. This response appears to include at least three components. First, the capillary endothelial cells of the renal tubule analog breach the basal lamina that surrounds an existing blood vessel; endothelial cells of the host during angiogenesis have been shown to secrete proteases, such as plasminogen activator, which enable them to digest their way through the basal lamina of the parent capillary or venule. Second, the host endothelial cells migrate toward the kidney cells. Third, the endothelial cells proliferate and form capillaries perfusing the glomeruli-like structure which forms at the proximal end of the renal tubule analogs. The resulting structure, termed a nephron analog is formed in vivo by implanting a renal tubule analog into a host and inducing glomeruli formation on the proximal end of the renal tubule analog. Glomeruli formation may be seen on the ends of some of the renal tubule analogs by two weeks post-implantation. At eight weeks post-implantation, glomeruli formation is extensive and visible on most renal tubule analogs.

The artificial renal unit precursor has the ability to induce the formation of neovasculature and may be implanted both in less vascularized or highly vascularized regions of a patient's body. One week after subcutaneous implantation, vascular formation is extensive along the length of the renal tubule analogs. The renal tubule analogs develop into nephron analogs by the end of eight (8) weeks by angiogenesis along the tubule and glomeruli formation in at least one region of the renal tubule analog. A plurality of glomeruli or glomeruli like structures are also seen on each renal tubule analog. Histological observations detected extensive vascularization along the length of each renal tubule analog.

The ARU examined show characteristics of proximal kidney tubules and glomeruli. ARUs express alkaline phosphatase and gamma glutamyl transferase, two genes which show almost exclusive expression in proximal tubule cells. Artificial glomeruli when tested functionally or immunohistochemically, show the presence of coagulation factor VIII.

Because a prosthetic kidney without a blood supply relies on diffusion for a supply of nutrients, a prosthetic kidney may be limited to a living layer not thicker than a few millimeters until angiogenesis can provide adequate perfusion. One embodiment of the invention is directed to a method to overcome this limitation by implanting multiple ARU structures into a host and allowing angiogenesis to connect the ARUs to an artery or a vein. Then the ARUs, along with an artery and vein are removed from the host and surgically combined into a larger or thicker ARU and reimplanted into a patient. The artery and vein of the ARU are connected to an artery and vein of the patient to provide a blood supply to the assembled prosthetic kidney.

Connection of the Effluent Channel

The effluent channel of the ARU may be connected to any location in a patient to allow removal of effluent from the prosthetic kidney. In an embodiment of the invention, the effluent channel may be connected to a part in the patient to allow removal of filtrate from the prosthetic kidney. The effluent channel may be connected to the urinary tract, including the kidney, the ureter, the renal pelvis, the bladder, the urethra, the testicle, prostate or vas differens. Alternatively, the effluent channel may be connected to the intestine, such as a large intestine or small intestine, in an intestinal conduit operation. Further, the effluent channel may be extended by a tube to protrude through the skin of the patient in whom the prosthetic kidney is implanted. In an abdominal implant of a prosthetic kidney, for example, the effluent channel may be extended through the abdominal wall. A cap may be installed on the end of the effluent channel to prevent leakage of effluent. When desired, the patient may remove the cap and allow effluent to be discharged externally.

The attachment of the effluent channel may be by sutures. In order that the ARU can be tailored by the surgeon installing the ARU in a patient, the effluent channel of different ARU may comprise different sizes so they can be matched to the effluent channel attachment site. Further, the effluent channel may be constructed of a material which would allow simple tailoring during an implant to fit the situation and location at the time of the operation.

In Vitro Operation

In another embodiment of the invention, the prosthetic kidney may be removed from the host along with its artery and vein and cultured in vitro. A prosthetic kidney with nephron analogs may be used as a bench top bioreactor to form a bench top prosthetic kidney. In vitro prosthetic kidneys may be fed using mammalian serums or by connection directly to a mammal. An initial pilot scale in vitro prosthetic kidney may be used as the starting material for an eventual production scale in vitro prosthetic kidney. For example, additional porous membrane structures may be attached to the prosthetic kidney to induce it to grow in size in culture. The in vitro prosthetic kidney may be eventually implanted into a patient as an individualized therapeutic product. The prosthetic kidney may be preserved and multiplied to such an extent in vitro that large scale industrial processing and harvest of a product may become possible. For example, an in vitro prosthetic kidney may be used to manufacture renin.

An embodiment of the invention is directed to the use of a prosthetic kidney for the analysis of the effects of a substance on the kidney. A substance may be a drug or pharmaceutical, a chemical, a microbe, a biological product, or an element. A drug or pharmaceutical is any chemical compound that may be used on or administered to a patient, including humans and animals, as an aid in the diagnosis, treatment, or prevention of disease or other abnormal condition. A drug may be used for the relief of pain of suffering, or to control or improve any physiologic or pathologic condition. Examples of drugs, include vaccines, recombinant agents, chemicals, recombinant nucleic acid, recombinant protein, and living, dead, or attenuated microbes. Useful drugs for testing include candidate drugs, chemicals, compounds and agents which are suspected to have properties of a drug. Chemicals which may be tested may include any chemical or substance a patient or a kidney may be exposed to. Such chemicals include environmental chemicals, personal hygiene products and cosmetics. Microbes include any living organism such as bacteria, fungus, viruses, amoeba, parasites, and yeast or the like which may be living, dead, in suspended animation, quiescent or attenuated at the time of testing. Biologicals products include products and waste products from living organisms such as proteins, lipids, nucleic acids, sugars, toxins which are produced from a living organism.

Treatment of Kidney Disease

In one embodiment of the invention, the prosthetic kidney may be maintained and operated externally and function ex vivo. A patient requiring blood treatment may connect their blood supply to the prosthetic kidney for a period of time. The treated blood may be separated from the prosthetic kidney following treatment and returned to the patient.

Another embodiment of the invention is directed to methods for treating kidney disease by the augmentation of kidney function by implanting the prosthetic kidney in the patient. Kidney disease is a general term that includes diseases ranging from less life threatening diseases such as kidney stones to more life-threatening disorders such as polycystic kidney disease and nephrosis, temporary and chronic and permanent kidney failure. Diseases of the kidney which may be treated by the method of the invention include any disease which may benefit from augmentation of renal function such as congenital anomalies of the kidney such as, cystic renal dysplasia, polycystic kidney disease, cystic diseases of renal medulla, acquired (dialysis-associated) cystic disease and simple cysts; glomerular diseases such as, acute glomerulonephritis, crescentic glomerulonephritis, nephrotic syndrome, membranous glomerulonephritis, minimal change disease, lipoid nephrosis, focal segmental glomerulosclerosis, membranoproliferative glomerulonephritis, IgA nephropathy, focal proliferative glomerulonephritis, chronic glomerulonephritis, systemic lupus erythematosus, Henoch-Schonlein purpura, bacterial endocarditis, diabetic glomerulosclerosis, amyloidosis and hereditary nephritis, tubule diseases such as acute tubular necrosis, acute renal failure, and other renal diseases such as, microangiopathic hemolytic anemia, atheroembolic renal disease, sickle cell disease nephropathy, diffuse cortical necrosis, renal infarcts, adenomas, carcinomas, nephroblastoma, immunologically mediated renal disease, drug induced nephritis, urate nephropathy, hypercalcemia and nephrocalcinosis.

Other diseases which may be treated may comprise any conditions where a patient's kidney may be damaged. For example, the method of the invention may be used to treat patients with healthy kidneys undergoing chemotherapy with a drug toxic to nephrons. Other conditions which may require treatment include, for example, trauma, toxin ingestion, autoimmune disease, old age, and the like.

The method of the invention is useful for the treatment of any kidney disease where it is desired to augment the function of a patient's normal kidneys. The prosthetic kidney may be implanted for a limited duration or permanently depending on whether the need for renal augmentation is temporary or permanent.

The prosthetic kidney may be of many different shapes to fit the needs of the patient and the implantation site. For example, a prosthetic kidney of an elongated or flat or compact shape may be optimal for abdominal or subcutaneous implantation where the patient's existing kidneys are not removed. Alternatively, a prosthetic kidney with the anatomic shape of a natural kidney may be most suited for patients who require kidney replacement. The size of the prosthetic kidney may also be varied for optimal performance. A larger patient may require a larger prosthetic kidney while a smaller patient, such as a child, may be more suited to a smaller prosthetic kidney.

Other embodiments and advantages of the invention are set forth, in part, in the description which follows and, in part, will be obvious from this description and may be learned from practice of the invention.

EXAMPLES

Example 1

Isolation of Kidney Cells

Small kidneys and kidney sections of large kidneys, such as from one week old C57 black mice, were decapsulated, dissected, minced and suspended in Dulbecco's Modified Eagles's Medium (DMEM; Sigma, St. Louis, Mo.) containing 15 mM Hepes, pH 7.4 and 0.5 µg/ml insulin, 1.0 mg/ml collagenase and 0.5 mg/ml dispase, a neutral protease from *Bacillus polymyxal* (Boehringer Mannheim, Indianapolis, Ind.).

Large kidneys, such as swine kidneys, were arterially perfused at 37° for 10 minutes with calcium free Eagles minimum essential medium within three hours of extraction. The kidneys were then perfused with 0.5 mg/ml collagenase (Type IV, Sigma, St. Louis, Mo.) in the same buffer supplemented with 1.5 mM $MgCl_2$ and 1.5 mM $CaCl_2$. The kidneys were then decapsulated, dissected, minced and suspended in Dulbecco's Modified Eagles's Medium (DMEM; Sigma, St. Louis, Mo.) containing 15 mM Hepes, pH 7.4 and 0.5 µg/ml insulin, 1.0 mg/ml collagenase and 0.5 mg/ml dispase, a neutral protease from *Bacillus polymyxal* (Boehringer Mannheim, Indianapolis, Ind.).

The kidney cell suspension, from either large or small kidneys, was gently agitated in a water bath for 30 minutes at 37° C. The cells and fragments were recovered by centrifugation at 50 g for five minutes. The pellets were resuspended in DMEM containing 10% fetal bovine serum (Biowhittaker, Walkersville, Md.) to stop proteolysis, and the turbid solution was passed through sterile 80 mesh nylon screens to eliminate large fragments. The cells were recovered by centrifugation and washed twice with calcium free Dulbecco's Modified Eagles's Medium.

Example 2

In vitro Culturing of Kidney Cells

Isolation of Rat Tail Collagen

Tendon was stripped from rat tails and stored in 0.12 M acetic acid in deionized water in 50 ml tubes. After 16 hours at 4° C. overnight.

Dialysis bags were pretreated to ensure a uniform pore size and removal of heavy metals. Briefly, the dialysis bag is submerged in a solution of 2% sodium bicarbonate and 0.05% EDTA and boiled for ten minutes. Multiple rinses of distilled water was used to remove the sodium bicarbonate and 0.05% EDTA.

The 0.12 M acetic acid solution comprising rat tendons was placed in treated dialysis bags and dialyzed for two or three days to remove acetic acid. The dialysis solution was changed every 3 to 4 hours.

Treatment of Porous Membrane Structure With Collagen

A porous membrane structure (FIG. 4) was treated by contact with a solution containing about 30 µg/ml collagen (Vitrogen or rat tail collagen), about 10 µg/ml human fibronectin (Sigma, St. Louis, Mo.) and about 10 µg/ml bovine serum albumin (Sigma, St. Louis, Mo.) in a total volume of about 2 ml of supplemented medium by incubation at 37° C. for 3 hours. Then the collagen coated porous membrane structure was placed into an incubator with 1 ml concentrated ammonium hydroxide (about 28% to about 30% $NH_4OH$, Sigma, St. Louis, Mo.) for 30 minutes to raise the pH and to promote the gelling of the collagen. After ammonium hydroxide treatment of the porous membrane structure, the structure was washed extensively with isotonic medium to neutralize the pH of the porous membrane structure before use.

Coating Tissue Culture Plates

The culture flasks, 75 $cm^2$, were coated with a solution containing about 30 µg/ml collagen (Vitrogen or rat tail collagen), about 10 µg/ml human fibronectin (Sigma, St. Louis, Mo.) and about 10 µg/ml bovine serum albumin (Sigma, St. Louis, Mo.) in a total volume of about 2 ml of supplemented medium by incubation at 37° C. for 3 hours.

Cell Culture

Digested single suspended renal cells were plated on a modified collagen matrix at a concentration of about $1 \times 10^6$ cells/ml and grown in DMEM supplemented with about 10% fetal bovine serum, about 5 µg/ml bovine insulin, about 10 µg/ml transferrin, about 10 µg/ml sodium selenite, about 0.5 µM hydrocortisone, about 10 ng/ml prostaglandin $E_2$, about 100 units/ml penicillin G, about 100 µg/ml streptomycin (Sigma, St. Louis, Mo.) in a 5% $CO_2$ incubator at about 37°.

Confluent monolayers were subcultured by treatment with about 0.05% trypsin, about 0.53 mM EDTA (Gibco BRL, Grand Island, N.Y.) in calcium ion free phosphate buffer saline (PBS) (about 1.51 mM $KH_2PO_4$, about 155.17 mM NaCl, about 2.8 mM $Na_2HPO \cdot 7H_2O$).

Cells may be cultured any time from the first passage by suspension in about 10% DMSO in culture medium for freezing and storage in liquid medium.

Example 3

Preparation of the Prosthetic Kidney

Kidney cells were cultured and expanded in vitro for 10 days. In vitro culture medium, DMEM supplemented with 10% fetal bovine serum, 5 µg/ml bovine insulin, 10 µg/ml transferrin, 10 µg/ml sodium selenite, 0.5 µM hydrocortisone, 10 ng/ml prostaglandin $E_2$, 100 units/ml penicillin G, 100 µg/ml streptomycin (Sigma, St. Louis, Mo.), was changed every other day. The cells were harvested by trypsin digestion using 0.05% trypsin, about 0.53 mM EDTA (Gibco BRL, Grand Island, N.Y.) in calcium ion free phosphate buffer saline (PBS) (about 1.51 mM $KH_2PO_4$, about 155.17 mM NaCl, about 2.8 mM $Na_2HPO \cdot 7H_2O$). After digestion for 10 minutes at 37° C. the cells were resuspended in DMEM media at approximately $5 \times 10^6$ cells/ml.

The cell suspension was gently layered onto a porous membrane structure comprising a preformed tubular device constructed from polycarbonate membrane with 4 micron pore size connected at one end with silastic catheter leading into a reservoir. The porous membrane structure was coated with rat collagen (Example 2). The porous membrane structure, layered with approximately $10^7$ cells per square centimeter of porous membrane surface was incubated at 37° C. under 5% $CO_2$ for about 30 minutes to about 40 minutes. At the end of the incubation period, additional prewarmed media, is gently added until the porous membrane structure is submerged. The porous membrane structure was incubated at 37° C. under 5% $CO_2$ for about 7 days to about 10 days. Media was changed and the cells were fed at frequent intervals such as for example, about every day, about every two days or about every three days.

At about seven to about 10 days after seeding, artificial renal unit precursors developed on the surface of the porous membrane structure. After 30 days of in vitro culture, a fluid was observed and collected at the reservoir of the porous membrane structure. While the in vitro culture media is red because of phenol red, the fluid in the reservoir is transparent and colorless. The collection of a fluid distinct from the media indicates that the artificial renal unit precursors exhibit filtration or secretion functions.

Implantation of Artificial Renal Unit Precursors

After about 7 to about 10 days after seeding, some of the porous membrane structures comprising artificial renal unit precursors on their surface were implanted in the subcutaneous space of athymic mice. Athymic mice may be purchased from commercially from suppliers such as Jackson Laboratories of Bar Harbor, Me. Animals were sacrificed at about two, about four, and about eight weeks post-implantation and the artificial renal unit precursors were retrieved and analyzed.

Figure 6:
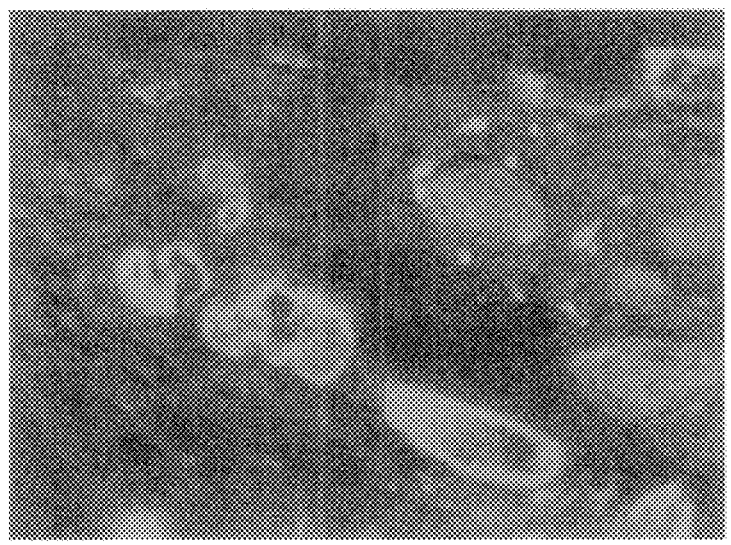
FIG. 6 depicts uniform staining for fibronectin in the extracellular matrix of newly formed tubules.

Retrieved specimens were examined grossly and histologically with hematoxylin and eosin. Inununohistochemical stains for osteopontin, fibronectin and alkaline phosphatase were performed to determine the cell types and their architecture in vivo (FIGS. 5, 6, 7). Human fibronectin monoclonal antibody (Sigmna, St. Louis, Mo.) was used against fibronectin matrix. Rhodarnine-conjugated goat anti-mouse (Boehringer Mannheim, Indianapolis, Ind.) was used as a secondary antibody. Immunocytochemical staining for osteopontin (FIG. 5) was performed with a polyclonal antibody produced in our laboratory. Antibodies were produced in New Zealand white rabbits using standard procedures (Harlow and Lane, *Antibodies a laboratory manual*, 1988, Cold Spring Harbor Press, Cold Spring Harbor) and used at a 1:5000 dilution ratio. Goat anti-rabbit antibody conjugated with FITC (Boehringer Mannheim, Indianapolis, Ind.) was used as a secondary antibody. Immunohistochemical stain for alkaline phosphatase using nitroblue tetrazolium and 5-Bromo-4-choloro-3-indolyl phosphate (Sigma, St. Louis, Mo.) was performed. Filtrate collected from the prosthetic kidney was straw yellow in color. Analysis of the filtrate for uric acid level was performed using a uric acid detection kit (Sigma Diagnostics, St. Louis, Mo.).

Figure 8A:
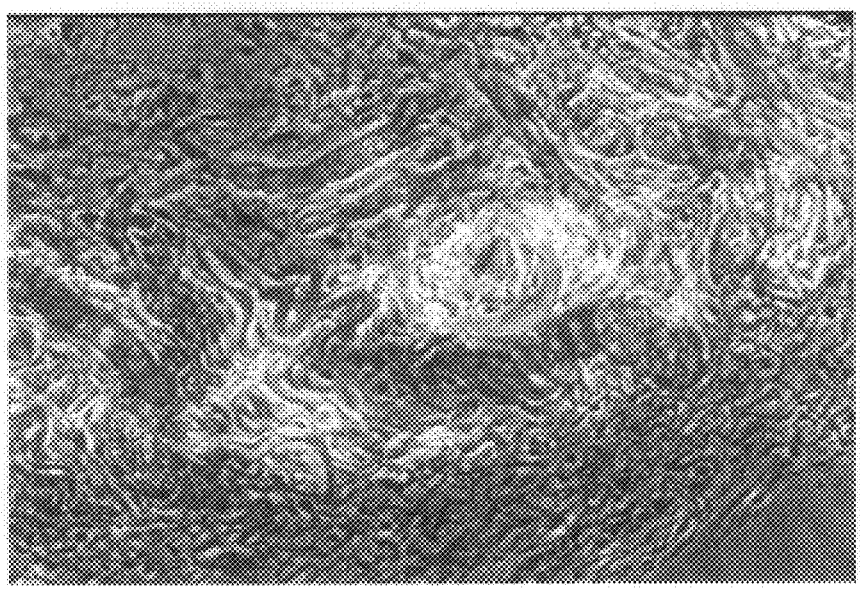
FIGS. 8A–B depict a section from an implanted ARU showing the formation of glomeruli-like structures and highly organized tubule-like structures of different sizes.
Figure 8B:
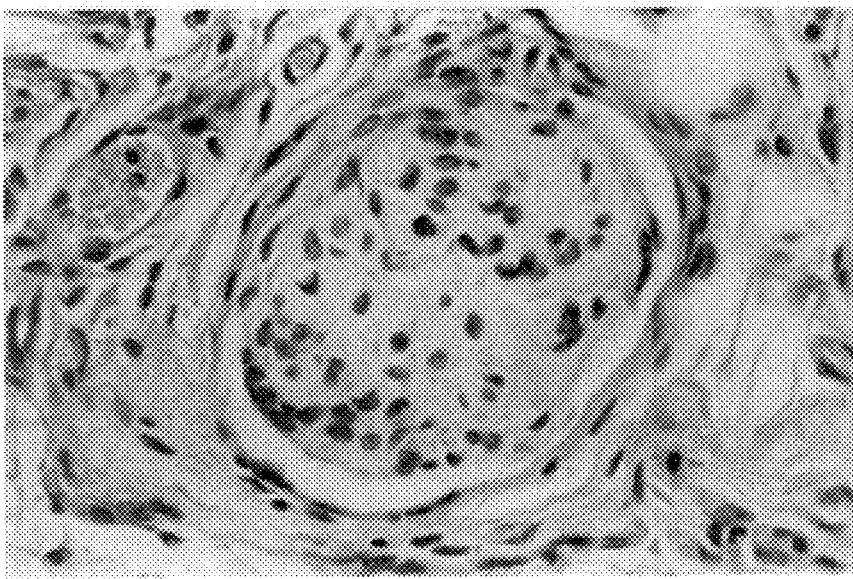

All animals survived until the sacrifice. Retrieved specimens maintained their original-architecture. The artificial renal units precursors were covered by host tissue grossly. The fluid in the prosthetic kidney was collected in the catheters connected to the membrane. Histological examination of the implanted prosthetic kidneys revealed extensive vascularization, formation of glomeruli (FIG. 8) and highly organized tubule-like structures. Immunocytochemical staining with anti-osteopontin antibody which is secreted primarily by proximal and distal tubule cells stained the tubular sections positively. Immunohistochemical staining for alkaline phosphatase stained proximal tubule like structures positively. Furthermore, uniform staining for fibronectin in the extracellular matrix of newly formed tubules was observed (FIG. 6). The yellow fluid collected from the newly formed renal unit contained 66 mg/dl uric acid, as compared to 2 mg/dl in plasma, suggesting that these tubules are capable of unidirectional secretion and concentration of uric acid. The evidence of glomeruti formation, the histological staining and the secretion of uric acid indicates that by 7 days post-implantation, the artificial renal unit precursor has developed into an ARU.

Phenotypical Comparison Between Renal Tubule Analogs and Natural Tubules

Proximal tubule cells of the kidney are cuboidal in shape. They contain a centrally placed round to oval nucleus with one or two prominent nucleoli. The apical surface of the cell is formed into long, slender finger-like microvilli which in animals such as the rat reach heights of 1.3 mm and increase apical surface area approximately 22-fold. In contrast the distal convoluted tubule usually contains short stubby microvilli on its apical surface and the collecting tubules lack a brush border.

The cells of the renal tubule analog resemble natural kidney tubules. Artificial kidney tubule cells have an extensive brush border of long slender microvilli which extend into the surface invaginations. The microvillar density of cultured cells is comparable to that found in proximal tubule cells in vivo. The lateral and basal borders of the proximal cells are highly irregular and show extensive interdigitations with adjacent cells similar to that observed in cultured cells.

One characteristic of proximal tubule cells is the presence of large numbers of lysosomes, phagosomes and peroxisomes also seen in large numbers in cultured cells. The maintenance of alkaline phosphatase and gamma glutamyl-transferase activities, marker enzymes for the brush border of proximal tubule cells, over long periods of culture provides further evidence for the identity and integrity of the artificial renal tubules.

Other embodiments and uses of the invention will be apparent to those skilled in the art from consideration of the specification and practice of the invention disclosed herein. All U.S. Patents and other references noted herein for whatever reason are specifically incorporated by reference. The specification and examples should be considered exemplary only with the true scope and spirit of the invention indicated by the following claims.

We claim:

1. A method for making a nephron analog comprising the steps of:
   (a) providing a porous membrane structure having an external surface defining an enclosed internal space having at least one effluent channel;
   (b) contacting said external surface with a suspension of kidney tissue cells;
   (c) culturing said kidney cells on said external surface in vitro to form a plurality of renal tubule analogs, each having a region for glomeruli structure formation, said renal tubule analogs comprising a three-dimensional aggregate of kidney tubule cells having a brush border configured to contact host tissue to induce formation of the glomeruli structure and a lumen in fluid communication with the enclosed space of said membrane structure; and
   (d) implanting said membrane structure having attached to said external surface thereof a plurality of renal tubule analogs into a host, whereby said renal tubule analog contacts host tissue and induces said host to produce glomeruli structures in at least one region of said renal tubule analog, thereby making a nephron analog.

2. The method of claim 1 wherein the brush border comprises a plurality of microvilli on the free surface of said kidney cell.

3. The method of claim 1 wherein the cell aggregates express osteopontin and the kidney tubule cells in at least one region of said aggregate express alkaline phosphatase.

4. The method of claim 1 wherein the cell aggregate is positive on a Periodic Acid Schiff staining assay.

5. The method of claim 1 wherein the renal tubule analogs express fibronectin.

6. The method of claim 1 wherein the kidney tubule cells are positive in a Periodic Acid Schiff assay.

7. The method of claim 1 wherein the kidney cells are fetal kidney cells or juvenile kidney cells.

8. The method of claim 1 wherein the kidney cells are from a kidney cortex.

9. The method of claim 1 wherein the kidney cells are human.

10. The method of claim 1 wherein the enclosed porous membrane structure prevents passage of cells and permits passage of fluid and gas.

11. The method of claim 1 wherein the enclosed porous membrane structure comprises pores of between about 0.04 micron to about 10 microns in diameter.

12. The method of claim 1 wherein the enclosed porous membrane structure comprises pores of between about 0.4 micron to about 4 microns in diameter.

13. A method for making a nephron analog comprising the steps of:
   a) isolating kidney tissue;
   b) disassociating said kidney tissue by enzymatic treatment to form a cell suspension;
   c) culturing said kidney cell suspension in vitro;
   d) treating an enclosed porous membrane structure with extracellular matrix protein;

e) culturing said kidney cells on the treated exterior surface of the enclosed porous membrane to form renal tubule analogs, each having a region for glomeruli structure formation, said renal tubule analogs comprising three-dimensional aggregates of kidney tubule cells having a brush border configured to contact host tissue to induce formation of the glomeruli structure and containing lumens within the interior of said aggregates; and f) implanting said membrane structure having attached to said external surface thereof a plurality of renal tubule analogs into a host, whereby said renal tubule analog contacts host tissue and induces said host to produce glomeruli structures in at least one region of said renal tubule analog, thereby making a nephron analog.

14. The method of claim 13 wherein the extracellular matrix protein comprises collagen.

15. The method of claim 13 wherein the collagen is rat tail collagen.

16. The method of claim 13 wherein the brush border compromises a plurality of micrbvilli on the free surface of said kidney cell.

17. The method of claim 13 wherein the cell aggregates express osteopontin and the kidney tubule cells in at least one region of said aggregate express alkaline phosphatase.

18. The method of claim 13 wherein the cell aggregate is positive on a Periodic Acid Schiff staining assay.

* * * * *

UNITED STATES PATENT AND TRADEMARK OFFICE
CERTIFICATE OF CORRECTION

PATENT NO. : 6,673,339 B1
DATED : January 27, 2004
INVENTOR(S) : Anthony Atala, James J. Yoo and Sammy Ashkar It is certified that error appears in the above-identified patent and that said Letters Patent is hereby corrected as shown below:

Column 26,
Line 6, "micrbvilli" should read -- microvilli --

Signed and Sealed this

Twenty-second Day of June, 2004

JON W. DUDAS
*Acting Director of the United States Patent and Trademark Office*